(12) United States Patent
Scheibe et al.

(10) Patent No.: US 10,709,870 B2
(45) Date of Patent: Jul. 14, 2020

(54) STEERABLE MEDICAL DEVICE AND METHOD (71) Applicant: Greatbatch Ltd., Clarence, NY (US)

(72) Inventors: Grant A. Scheibe, Loretto, MN (US); Travis White, Rockford, MN (US)

(73) Assignee: Greatbatch Ltd., Clarence, NY (US)

( * ) Notice: Subject to any disclaimer, the term of this patent is extended or adjusted under 35 U.S.C. 154(b) by 191 days.

(21) Appl. No.: 15/917,953

(22) Filed: Mar. 12, 2018

(65) Prior Publication Data
US 2018/0264231 A1 Sep. 20, 2018

Related U.S. Application Data (60) Provisional application No. 62/471,003, filed on Mar. 14, 2017.

(51) Int. Cl.
*A61M 25/01* (2006.01)
*A61B 8/12* (2006.01)

(52) U.S. Cl.
CPC .... *A61M 25/0147* (2013.01); *A61M 25/0133* (2013.01); *A61M 25/0136* (2013.01); *A61B 8/12* (2013.01); *A61M 2025/015* (2013.01)

(58) Field of Classification Search
CPC .......... A61M 25/0147; A61M 25/0136; A61M 25/0133; A61M 2025/015
See application file for complete search history.

(56) References Cited

U.S. PATENT DOCUMENTS

| 6,228,032 | B1 * | 5/2001 | Eaton ............... A61B 1/0052 600/463 |
| 7,691,095 | B2 | 4/2010 | Bednarek et al. |
| 8,308,659 | B2 | 11/2012 | Scheibe et al. |
| 8,556,850 | B2 | 10/2013 | Tegg et al. |
| 8,676,290 | B2 | 3/2014 | Tegg et al. |
| 9,149,607 | B2 | 10/2015 | Scheibe et al. |
| 9,289,147 | B2 | 3/2016 | Tegg et al. |
| 9,764,115 | B2 | 9/2017 | Tegg et al. |
| 9,861,787 | B2 | 1/2018 | Tegg |
| 2011/0282176 | A1 | 11/2011 | Tegg |
| 2012/0041387 | A1 * | 2/2012 | Bruggemann .... A61M 5/14546 604/218 |

(Continued)

OTHER PUBLICATIONS

Extended European Search Report, Application No. 18161825.7 dated Aug. 14, 2018.

*Primary Examiner* — Nilay J Shah
(74) *Attorney, Agent, or Firm* — Michael P. Horvath (57) ABSTRACT

In various examples, a system includes a steerable medical device including a handle including a longitudinal axis. An elongate shaft extends distally from the handle. The elongate shaft includes a distal tip and a lumen through the elongate shaft. At least four pullwires are disposed within the handle and extending to and anchored proximate the distal tip of the elongate shaft. At least two actuators are associated with the handle. The at least two actuators are operably coupled to the at least four pullwires with actuation of the first actuator causing tension in the first or second pullwire to deflect the distal tip in a first or second tip direction, respectively, and actuation of the second actuator causing tension in the third or fourth pullwire to deflect the distal tip in a third or fourth tip direction, respectively.

20 Claims, 8 Drawing Sheets

(56) References Cited

U.S. PATENT DOCUMENTS

2012/0089125 A1* 4/2012 Scheibe ............ A61M 25/0136
 604/523
2016/0074625 A1 3/2016 Furnish
2016/0279386 A1 9/2016 Dale et al.

* cited by examiner

STEERABLE MEDICAL DEVICE AND METHOD

CROSS REFERENCE TO RELATED APPLICATIONS

This application claims the benefit of priority to U.S. Provisional Application Ser. No. 62/471,003, filed on Mar. 14, 2017, entitled "CATHETER STEERING HANDLE," which is incorporated by reference herein in its entirety.

BACKGROUND

The present invention relates to a steerable device, and more specifically relates to a medical device that is steerable in multiple directions.

In various medical procedures, steerable catheters or other devices can allow for navigation to a location within a patient and/or articulation within the patient in order to access the location and/or achieve a particular orientation or series of orientations within the patient. In many cases, such devices include limited degrees of motion, making it difficult to achieve particular orientations and or locations. In turn, such devices make some medical procedures more difficult than the medical procedures would otherwise be with a device having more degrees of motion.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used with respect to a medical device with multidirectional steering capability. In various examples, the present subject matter can be used with a device, an apparatus, a system, and/or a method to provide for increased maneuverability within a patient. The present inventors have recognized that the present subject matter can be used to provide a catheter or other medical device with multiple degrees of motion to allow for a tip of the device having a 360-degree range of deflection. To better illustrate the apparatuses, systems, and methods described herein, a non-limiting list of examples is provided here:

Example 1 can include subject matter that can include a steerable medical device including a handle including a longitudinal axis. An elongate shaft extends distally from the handle. The elongate shaft includes a distal tip and a lumen through the elongate shaft. At least four pullwires are disposed within the handle and extend to and are anchored proximate the distal tip of the elongate shaft. The at least four pullwires include a first pullwire, a second pullwire, a third pullwire, and a fourth pullwire. At least two actuators are associated with the handle. The at least two actuators include a first actuator and a second actuator. The at least two actuators are operably coupled to the at least four pullwires. Actuation of the first actuator in a first actuator direction causes tension in the first pullwire and deflection of the distal tip in a first tip direction. Actuation of the first actuator in a second actuator direction causes tension in the second pullwire and deflection of the distal tip in a second tip direction substantially opposite the first tip direction. Actuation of the second actuator in a first actuator direction causes tension in the third pullwire and deflection of the distal tip in a third tip direction different from the first tip direction and the second tip direction. Actuation of the second actuator in a second actuator direction causes tension in the fourth pullwire and deflection of the distal tip in a fourth tip direction substantially opposite the third tip direction.

In Example 2, the subject matter of Example 1 is optionally configured such that the at least four pullwires extend within the elongate shaft to proximate the distal tip of the elongate shaft.

In Example 3, the subject matter of any one of Examples 1-2 is optionally configured such that the first actuator is rotatable about the longitudinal axis of the handle.

In Example 4, the subject matter of any one of Examples 1-3 is optionally configured such that the second actuator is rotatable about the longitudinal axis of the handle.

In Example 5, the subject matter of any one of Examples 1-4 is optionally configured such that the first actuator and the second actuator are each independently rotatable about the longitudinal axis of the handle.

In Example 6, the subject matter of any one of Examples 1-5 optionally includes a first threaded member disposed within the handle and movable with actuation of the first actuator. The first threaded member is operably coupled to the first and second pullwires, wherein movement of the first threaded member causes tension in at least one of the first pullwire and the second pullwire.

In Example 7, the subject matter of Example 6 is optionally configured such that actuation of the first actuator causes rotation of the first threaded member.

In Example 8, the subject matter of Example 7 optionally includes a first drive nut theadably coupled to the first threaded member. The first and second pullwires are operably coupled to the first drive nut, wherein rotation of the first threaded member causes translation of the first drive nut along the longitudinal axis of the handle and, in turn, tension in at least one of the first pullwire and the second pullwire.

In Example 9, the subject matter of Example 8 is optionally configured such that proximal translation of the first drive nut causes tension in the first pullwire and distal translation of the first drive nut causes tension in the second pullwire.

In Example 10, the subject matter of Example 9 optionally includes a first U-shaped member configured to change a direction of the second pullwire. The second pullwire extends proximally from the first drive nut to the first U-shaped member, around the first U-shaped member, and distally from the first U-shaped member to proximate the distal tip of the elongate shaft.

In Example 11, the subject matter of any one of Examples 6-10 optionally includes a second threaded member disposed within the handle and movable with actuation of the second actuator. The second threaded member is operably coupled to the third and fourth pullwires, wherein movement of the second threaded member causes tension in at least one of the third pullwire and the fourth pullwire.

In Example 12, the subject matter of Example 11 is optionally configured such that actuation of the second actuator causes rotation of the second threaded member.

In Example 13, the subject matter of Example 12 optionally includes a second drive nut theadably coupled to the second threaded member. The third and fourth pullwires are operably coupled to second drive nut, wherein rotation of the second threaded member causes translation of the second drive nut along the longitudinal axis of the handle and, in turn, tension in at least one of the third pullwire and the fourth pullwire.

In Example 14, the subject matter of Example 13 is optionally configured such that proximal translation of the second drive nut causes tension in the third pullwire and distal translation of the second drive nut causes tension in the fourth pullwire.

In Example 15, the subject matter of Example 14 optionally includes a second U-shaped member configured to change a direction of the fourth pullwire. The fourth pullwire extends proximally from the second drive nut to the second U-shaped member, around the second U-shaped member, and distally from the second U-shaped member to proximate the distal tip of the elongate shaft.

In Example 16, the subject matter of any one of Examples 11-15 is optionally configured such that the first threaded member at least partially overlaps the second threaded member. The second threaded member is disposed at least partially within the first threaded member.

Example 17 can include, or can optionally be combined with any one of Examples 1-16 to include subject matter that can include a steerable medical device including a handle including a longitudinal axis. An elongate shaft extends distally from the handle. The elongate shaft includes a distal tip and a lumen through the elongate shaft. At least four pullwires are disposed within the handle and extend to and are anchored proximate the distal tip of the elongate shaft. The at least four pullwires include a first pullwire, a second pullwire, a third pullwire, and a fourth pullwire. At least two actuators are associated with the handle. The at least two actuators include a first actuator and a second actuator. At least two threaded members are disposed within the handle. The at least two threaded members include a first threaded member and a second threaded member. The first threaded member is movable with actuation of the first actuator, and the second threaded member is movable with actuation of the second actuator. At least two drive nuts are disposed within the handle. The at least two drive nuts include a first drive nut and a second drive nut. The first drive nut is theadably coupled to the first threaded member and translatable along the longitudinal axis of the handle with movement of the first threaded member. The second drive nut is theadably coupled to the second threaded member and translatable along the longitudinal axis of the handle with movement of the second threaded member. The first and second pullwires are operably coupled to the first drive nut, and the third and fourth pullwires are operably coupled to the second drive nut. Actuation of the first actuator in a first actuator direction causes tension in the first pullwire and deflection of the distal tip in a first tip direction. Actuation of the first actuator in a second actuator direction causes tension in the second pullwire and deflection of the distal tip in a second tip direction substantially opposite the first tip direction. Actuation of the second actuator in a first actuator direction causes tension in the third pullwire and deflection of the distal tip in a third tip direction different from the first tip direction and the second tip direction. Actuation of the second actuator in a second actuator direction causes tension in the fourth pullwire and deflection of the distal tip in a fourth tip direction substantially opposite the third tip direction.

In Example 18, the subject matter of Example 17 is optionally configured such that proximal translation of the first drive nut causes tension in the first pullwire and distal translation of the first drive nut causes tension in the second pullwire. Proximal translation of the second drive nut causes tension in the third pullwire and distal translation of the second drive nut causes tension in the fourth pullwire.

In Example 19, the subject matter of any one of Examples 17-18 is optionally configured such that the first threaded member at least partially overlaps the second threaded member. The second threaded member is disposed at least partially within the first threaded member.

In Example 20, the subject matter of any one of Examples 17-19 is optionally configured such that the first actuator and the second actuator are each independently rotatable about the longitudinal axis of the handle.

DETAILED DESCRIPTION

The present patent application relates to a device, an apparatus, a system, and a method for providing multidirectional steering capability. In various examples, as described herein, the device, apparatus, system, and method can include multiple degrees of motion to allow for increased maneuverability within a patient. The present inventors have recognized that, in some examples, the present subject matter can be used to provide a device with multiple degrees of motion to allow for a tip of the device having a 360-degree range of deflection. In some examples, the device can include a medical device, such as, but not limited to a catheter, a sheath, an introducer, a guidewire, or the like.

In various medical procedures, it can be desirable to have a medical device that includes a tip that can articulate in multiple directions, such as, for instance, a 360-degree range of deflection. Medical procedures for which such a device would be helpful include, but are not limited to, an intravascular ultrasound (IVUS) procedure. In some examples, a catheter handle mechanism configured to articulate four individual pullwires can be used to achieve this range of motion. Additionally, in some examples, such a medical device can be used with one hand to steer the distal end of the medical device. In various examples, such a handle mechanism can be used in any steerable/deflectable catheter, therapy device, or other medical device.

The following co-owned applications relate to steerable medical devices and are hereby incorporated by reference in their entireties: U.S. application Ser. No. 12/463,570, now U.S. Pat. No. 8,308,659, filed May 11, 2009 and entitled "BI-DIRECTIONAL SHEATH DEFLECTION MECHANISM"; and U.S. application Ser. No. 13/269,858, now U.S. Pat. No. 9,149,607, filed Oct. 10, 2011 and entitled "BI-DIRECTIONAL CATHETER STEERING HANDLE."

Figure 1:
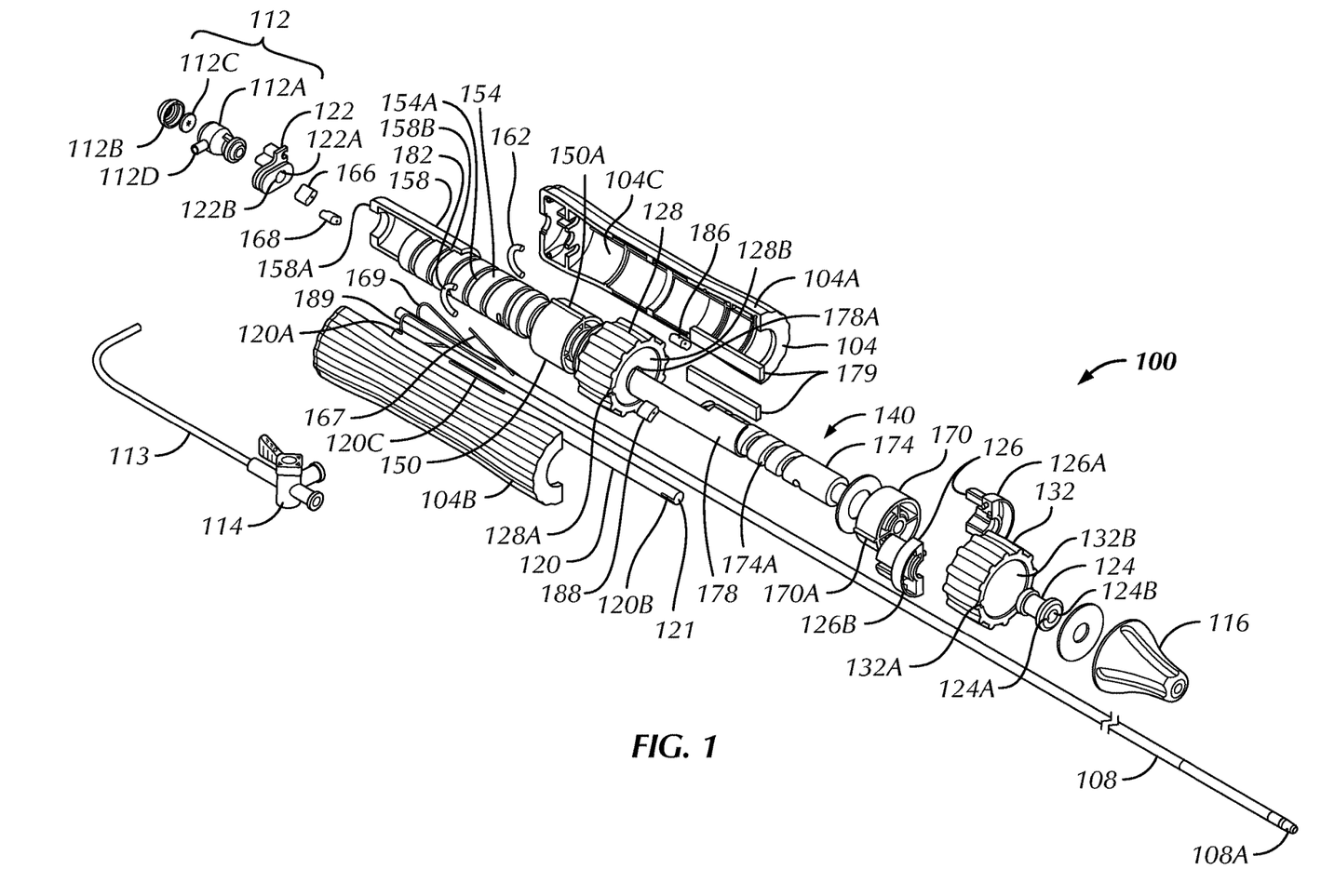
FIG. 1 is an exploded perspective view of a steerable medical device in accordance with at least one example of the invention.
Figure 2:
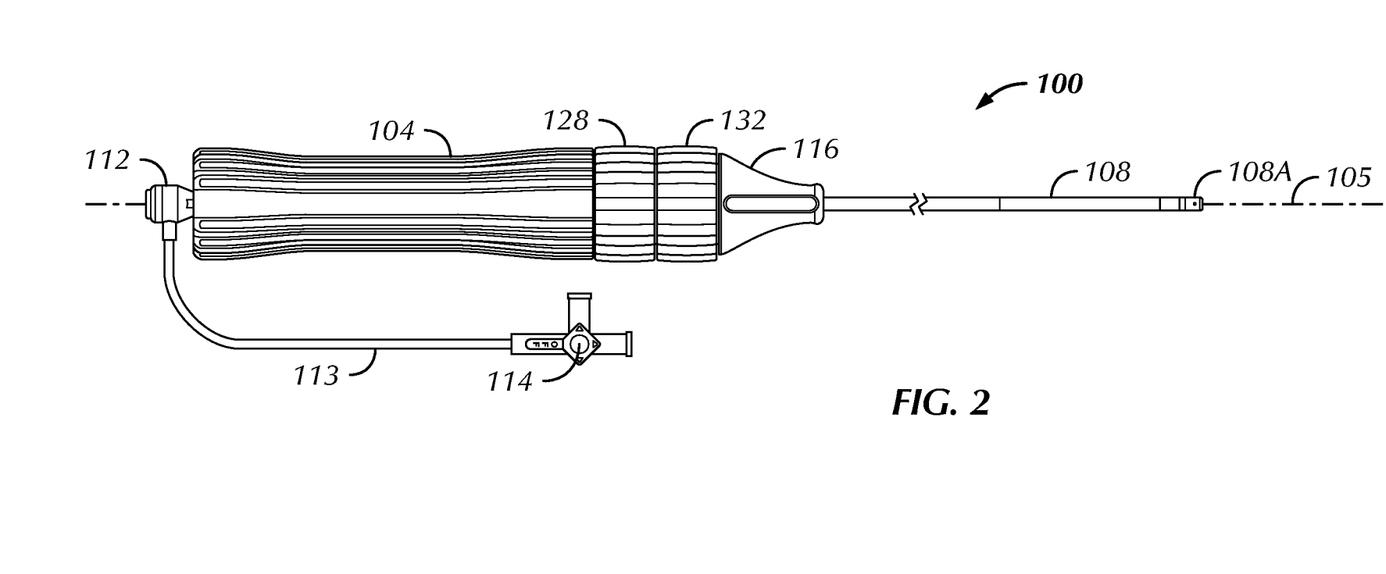
FIG. 2 is a side view of the steerable medical device of FIG. 1.
Figure 3:
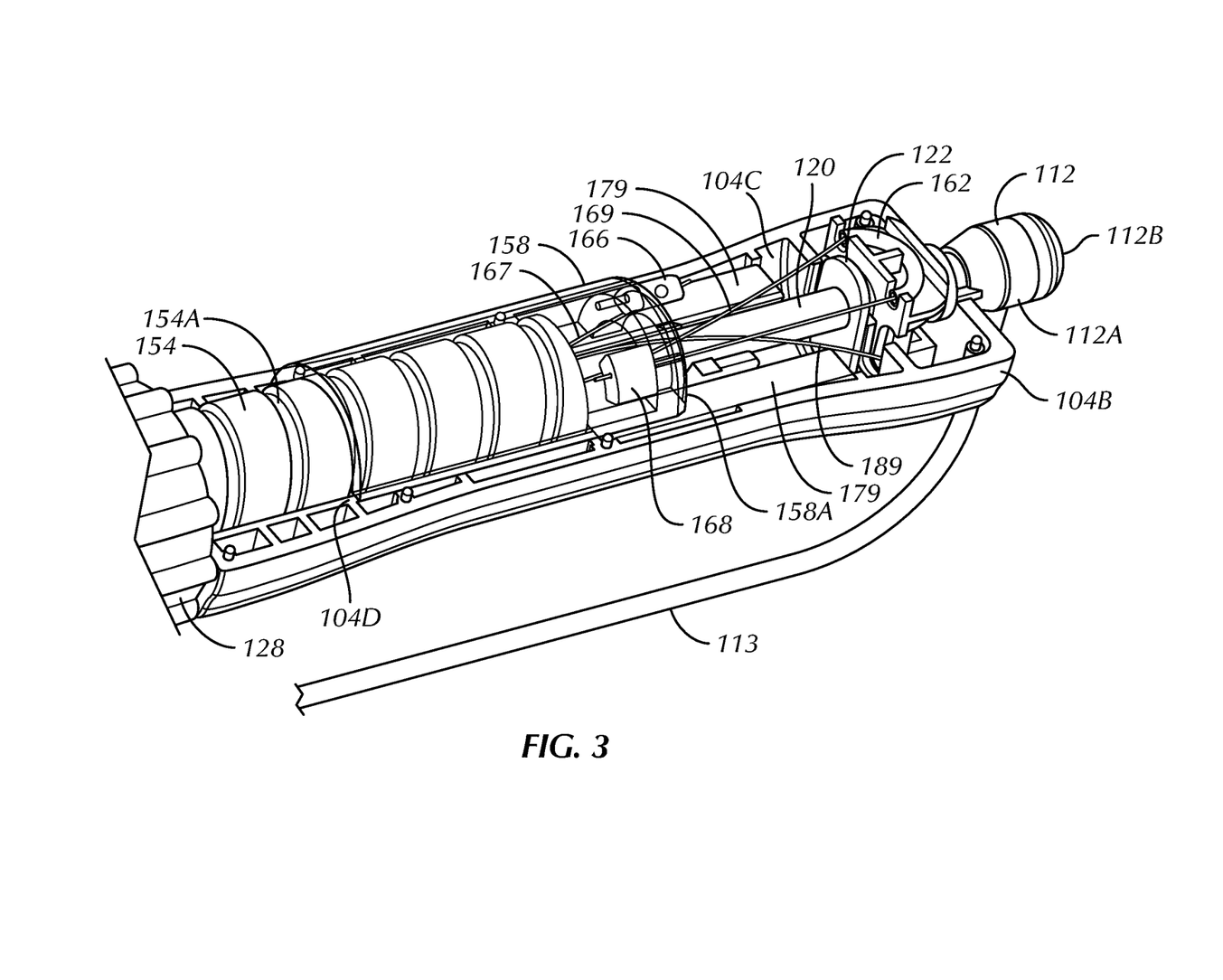
FIG. 3 is a proximally-facing perspective view of a handle of the steerable medical device of FIG. 1, the handle having part of a handle housing removed.
Figure 4:
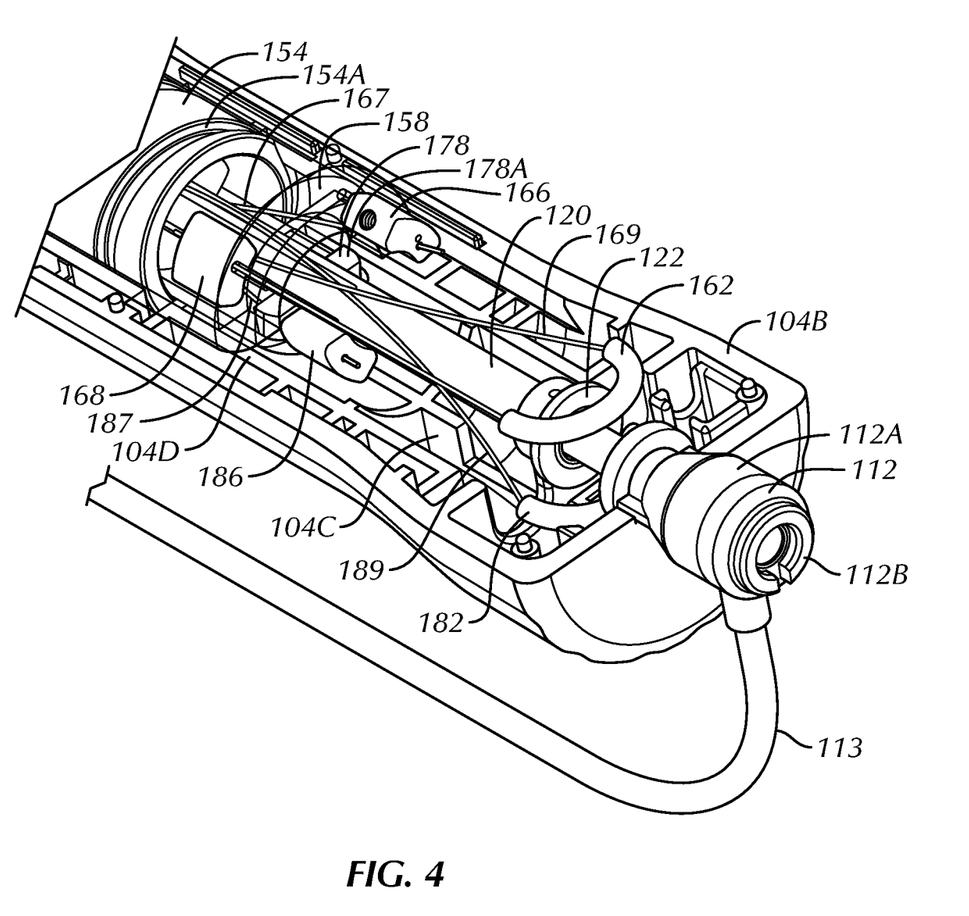
FIG. 4 is a distally-facing perspective view of the handle of FIG. 3, the handle having part of the handle housing removed.
Figure 5:
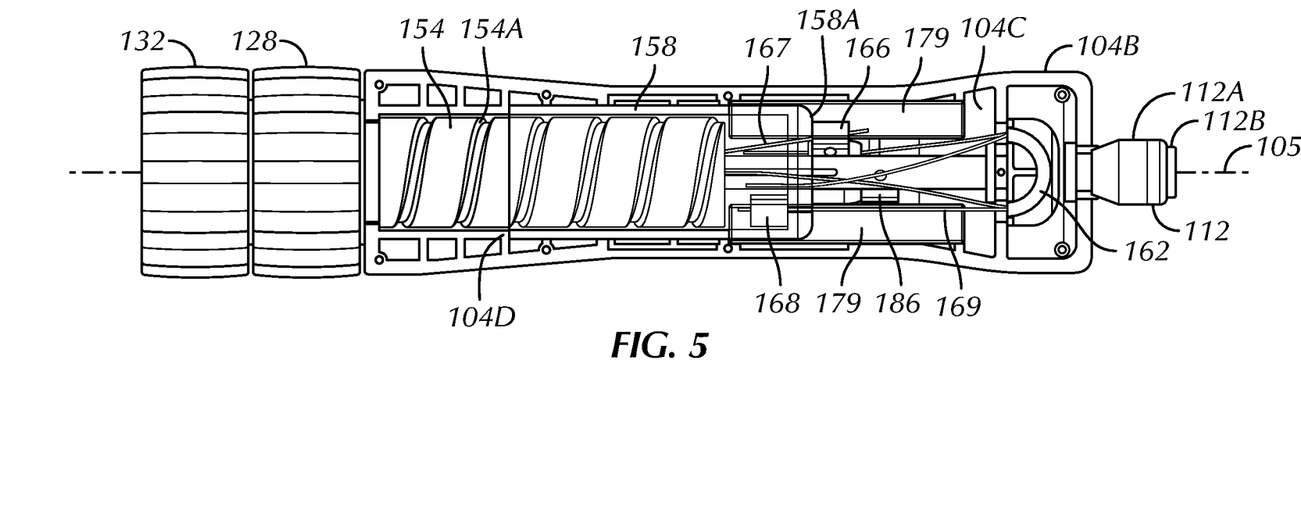
FIG. 5 is a side elevational view of the handle of FIG. 3, the handle having part of the handle housing removed.
Figure 6:
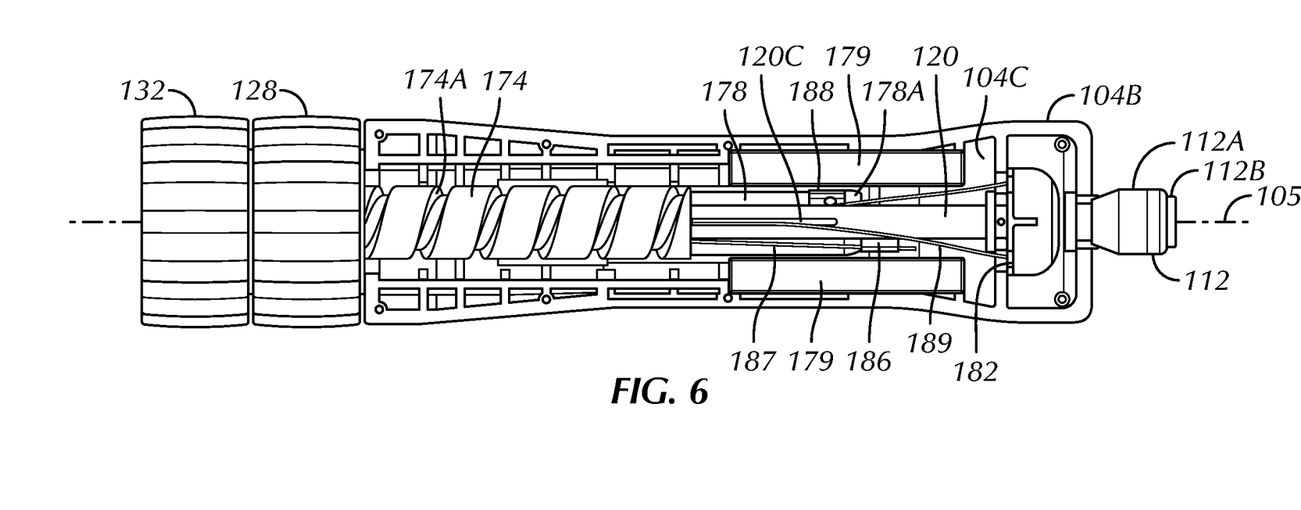
FIG. 6 is a side elevational view of the handle of FIG. 3, the handle having part of the handle housing and some internal components of the handle removed.

Referring now to FIGS. 1 and 2, in some examples, a steerable medical device 100 is configured to provide multiple degrees of motion to facilitate navigation and/or articulation of the steerable medical device 100 within a patient. For instance, in some examples, the steerable medical device 100 includes a 360-degree range of deflection. In some examples, the steerable medical device 100 includes a handle 104 including a longitudinal axis 105. In some examples, the handle 104 includes two handle portions 104A, 104B that are coupled together to enclose at least a portion of a handle mechanism 140 (described in greater detail below) within the handle 104. Although shown and described herein as halving two portions 104A, 104B, in other examples, the handle 104 can include fewer or more than two portions, provided the handle mechanism 140 is able to be placed within the handle 104. In some examples, the handle portions 104A, 104B can be coupled together in various ways, including, but not limited to, the handle portions 104A, 104B being configured to be snap fit or otherwise frictionally engaged together; the handle portions 104A, 104B being welded (ultrasonic, vibration, laser, or the like) together; the handle portions 104A, 104B being adhered together using an adhesive (epoxy, silicone, polyurethane, or the like); or a combination thereof. In some examples, the handle portions 104A, 104B are shaped and sized to allow for at least a portion of the handle mechanism 140 to be housed within an interior 104C of the handle 104 with the handle portions 104A, 104B coupled together.

In some examples, the steerable medical device 100 includes an elongate shaft 108 extending distally from the handle 104. The elongate shaft, in some examples, includes a distal tip 108A and a lumen 108B (see FIG. 7) through the elongate shaft 108. In some examples, the elongate shaft 108 extends from a distal end of the handle 104. In some examples, at least a portion of the elongate shaft 108 is disposed within the handle 104. In further examples, the elongate shaft 108 extends from a valve member 112 disposed at a proximal end of the handle 104, through the handle 104, and out of the distal end of the handle 104. The elongate shaft 108, in some examples, can include an over-molded hub on a proximal end of the elongate shaft 108 with keying ribs that secure the hub and, in turn, the elongate shaft 108 within the handle 104.

The valve member 112, in some examples, includes a valve housing 112A engageable with the handle 104, for instance, within the proximal end of the housing 104. The valve member 112, in some examples, includes a valve cap 112B disposed at a proximal end of the valve housing 112A and capturing a valve 112C between the valve cap 112B and the valve housing 112A. The valve 112C, in some examples, is configured to limit expelling of fluid (for instance, a bodily fluid, a fluid introduced for the procedure, or a combination of the two) to allow insertion of an introducible device (such as, for instance, a guidewire, a catheter, a delivery device, a sensing device, an ablation device, or another medical device) into the steerable medical device 100. In some examples, it is contemplated that the valve member 112 need not include a valve 112C, for instance, when fluid being expelled from the device 100 is not an issue. In this way, in some examples, the valve member 112 allows insertion of the introducible device into the steerable medical device 100 and through the elongate shaft 108 to a location within a patient. In some examples, the valve member 112 can include a sideport 112D in the valve housing 112A. The sideport 112D, in some examples, allows for a tube 113 and/or stopcock 114 to fluidly couple to the valve member 112 to allow for introduction of a fluid (such as, but not limited to, saline, water, air, and/or nitrogen) or connection to a suction device, for stance, to remove a bodily fluid from within the patient and/or the steerable medical device 100. In other examples, the valve member 112 need not include a sideport if introduction and/or removal of one or more fluids is not necessary for the steerable medical device 100.

In some examples, the elongate shaft 108 extends through a nose member 116 disposed at the distal end of the handle 104. The nose member 116, in some examples, provides strain relief for the elongate shaft 108. In some examples, the nose member 116 is substantially conically shaped, although this is not intended to be limiting. As such, in various examples, other shapes of the nose member 116 are contemplated herein.

In some examples, a support tube 120 is disposed within the handle 104. In some examples, the support tube 120 includes a lumen 121 through the support tube 120 sized and shaped to accept a portion of the elongate shaft 108 therein. The support tube 120, in some examples, is formed from a rigid material such as, but not limited to, plastic, metal, or the like. In some examples, the support tube 120 includes one or more windows 120C formed in the support tube 120. In some examples, the support tube 120 includes four windows 120C. In further examples, the support tube 120 includes four windows 120C formed in the support tube 120 and equidistantly spaced from one another around a circumference of the support tube 120.

In some examples, the support tube 120 includes a proximal notch 120A formed in a proximal end of the support tube 120 and a distal notch 120B formed in a distal end of the support tube 120. In some examples, the proximal notch 120A is configured to accept a key 122A of a proximal insert 122 when the proximal end of the support tube 120 is placed within an opening 122B of the proximal insert 122. In this way, interaction between the proximal notch 120A of the support tube 120 and the key 122A of the proximal insert 122 inhibits rotation of the support tube 120 relative to the proximal insert 122. The proximal insert 122, in some examples, is configured to engage with the handle 104 to inhibit rotation of the proximal insert 122 relative to the handle 104. In some examples, the distal notch 120B is configured to accept a key 124A of a distal support 124 when the distal end of the support tube 120 is placed within an opening 124B of the distal support 122. In this way, interaction between the distal notch 120B of the support tube 120 and the key 124A of the distal support 124 inhibits rotation of the support tube 120 relative the distal support 124. In this way, in some examples, each of the handle 104, the support tube 120, the proximal insert 122, and the distal support 124 are engaged with one another and inhibited from rotating with respect to one another. In some examples, the nose member 116 is configured to engage with the distal support

124. In some examples, the nose member 116 is configured to snap onto the distal support 124.

In some examples, the support tube 120 provides central support to the handle 104 and the handle mechanism 140. In some examples, the support tube 120 allows components of the handle mechanism 140 to rotate about an outer diameter of the support tube 120 while inhibiting the nose member 116 from rotating.

In some examples, at least two actuators 128, 132 are associated with the handle 104. In some examples, the at least two actuators 128, 132 include a first actuator 128 and a second actuator 132. In other examples, the at least two actuators 128, 132 include more than two actuators to allow for increased control of the device 100 or aspects of the device 100 if desirable for the particular application of the device 100. In some examples, at least one of the two actuators 128, 132 is rotatable about the longitudinal axis 105 of the handle 104. That is, in some examples, the first and second actuators 128, 132 include knobs that are rotatable with respect to the handle 104 about the longitudinal axis 105 to control the device 100 (for instance, to control deflection of the distal tip 108A of the elongate shaft 108 of the device 100). While the first and second actuators 128, 132 are shown as knobs herein, in other examples, it is contemplated that the first and second actuators 128, 132 include a slider, a toggle switch, a knob rotatable about an axis other than the longitudinal axis 105, or a combination of two different types of actuators, provided the first and second actuators 128, 132 are capable of controlling the device 100 to perform the particular function of the device 100. In some examples, the first actuator 128 and the second actuator 132 are each independently rotatable about the longitudinal axis 105 of the handle 104. That is, rotation of one of the first and second actuators 128, 132 does not cause rotation of the other of the first and second actuators 128, 132, thereby allowing independent control of each of the first and second actuators 128, 132 by the physician or other user.

Referring to FIGS. 1-7, at least four pullwires 167, 169, 187, 189, in some examples, are disposed within the handle 104 and extend to and are anchored proximate the distal tip 108A of the elongate shaft 108. In some examples, the at least four pullwires 167, 169, 187, 189 include a first pullwire 167, a second pullwire 169, a third pullwire 187, and a fourth pullwire 189. In some examples, the at least four pullwires 167, 169, 187, 189 extend within the elongate shaft 108 to proximate the distal tip 108A of the elongate shaft 108. In some examples, the at least four pullwires 167, 169, 187, 189 are operably coupled to the first and second actuators 128, 132, such that actuation of the first actuator 128 and/or the second actuator 132 causes tension in at least one of the at least four pullwires 167, 169, 187, 189, thereby causing the distal tip 108A of the elongate shaft 108 to deflect, as will be described in more detail below. In some examples, the handle mechanism 140 is configured to cause deflection of the distal tip 108A of the elongate shaft 108 with actuation of the first actuator 128 and/or the second actuator 132.

Figure 7:
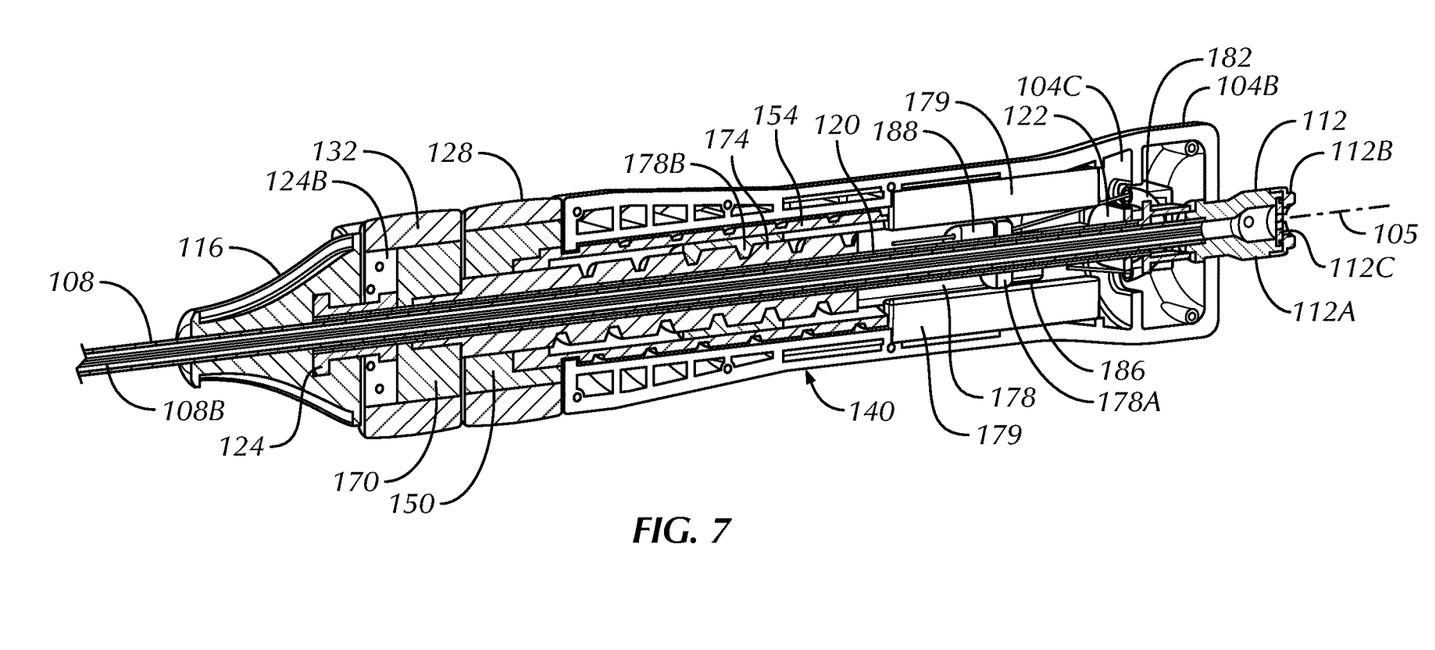
FIG. 7 is a perspective cross-sectional view of the handle of FIG. 3.
Figure 8:
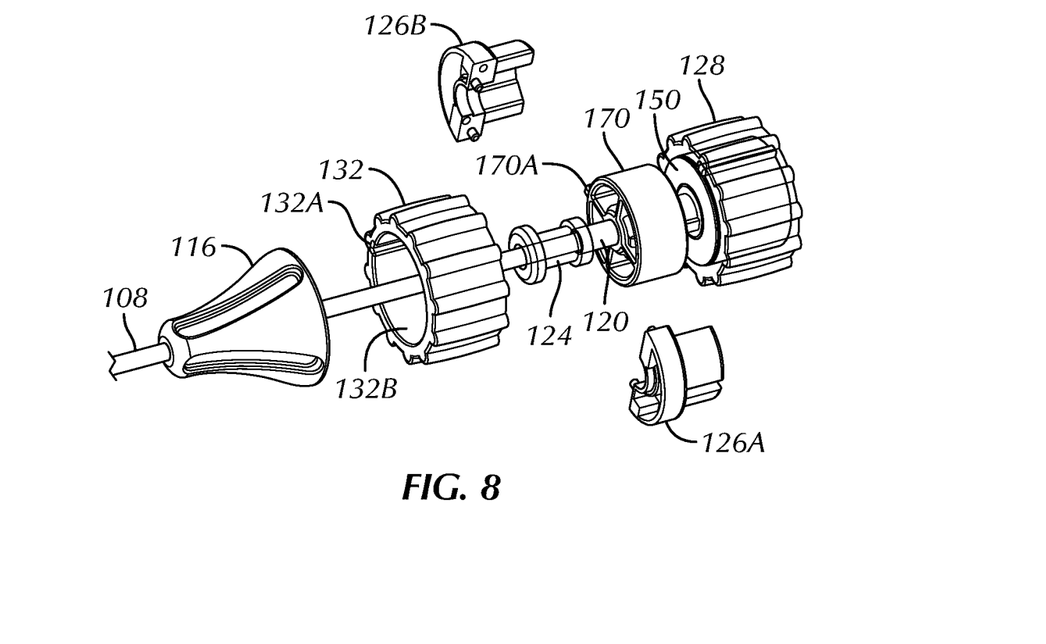
FIG. 8 is an exploded perspective view of a distal end the handle of FIG. 3.
Figure 9:
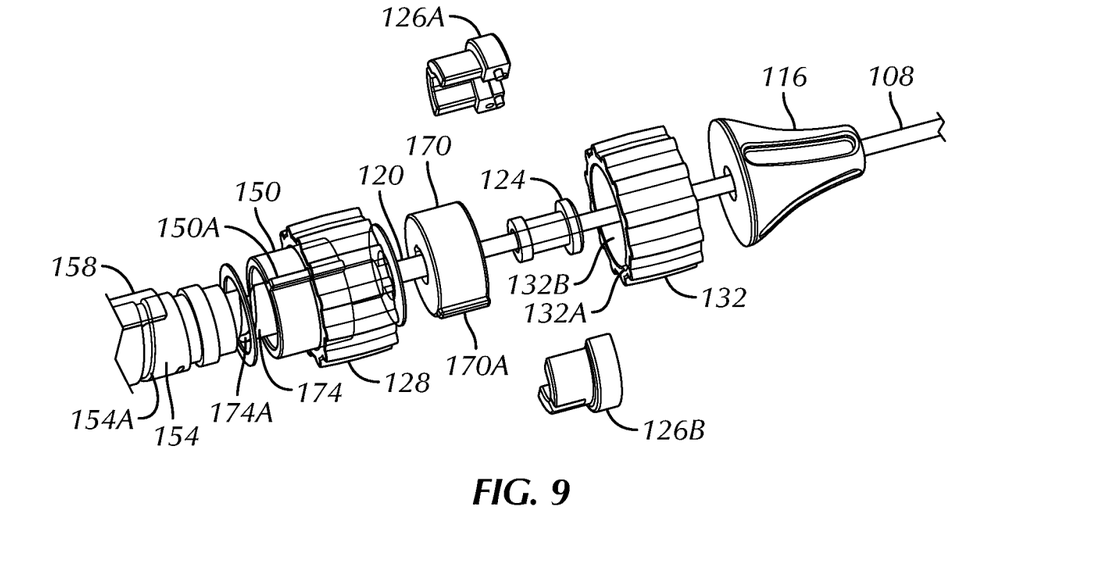
FIG. 9 is an exploded perspective view of a distal end the handle of FIG. 3.

In some examples, the first, second, third, and fourth pullwires 167, 169, 187, 189 extend out from the elongate shaft 108 within the handle 104 in order to operably couple with the first and second actuators 128, 132. Because, in some examples, the support tube 120 is disposed over the elongate shaft 108, the support tube 120 can include one or more windows 120C formed in a sidewall of the support tube 120 at one or more locations around the support tube 120 to allow for the first, second, third, and fourth pullwires 167, 169, 187, 189 to extend out from the elongate shaft 108 and the support tube 120 to the handle mechanism 140 in order to operably couple the first, second, third, and fourth pullwires 167, 169, 187, 189 to the first and second actuators 128, 132. In some examples, the support tube 120 includes four windows 120C disposed around the support tube 120, such that each of the first, second, third, and fourth pullwires 167, 169, 187, 189 exits through its own window 120C in the support tube 120. In other examples, the support tube 120 can include fewer than four windows 120C, such that one or more of the first, second, third, and fourth pullwires 167, 169, 187, 189 share at least one of the windows 120C.

In some examples, the handle mechanism 140 includes a first threaded member 154 disposed within the handle 104 and movable with actuation of the first actuator 128. In some examples, the first threaded member 154 includes at least one thread 154A disposed in an outer surface of the first threaded member 154. The first threaded member 154, in some examples, is operably coupled to the first and second pullwires 167, 169, such that movement of the first threaded member 154 causes tension in at least one of the first pullwire 167 and the second pullwire 169. In some examples, rotation of the first actuator 128 causes rotation of the first threaded member 154. In some examples, the first actuator 128 is coupled directly to the first threaded member 154. In some examples, the first actuator 128 is coupled to a first drive ring 150, and the first drive ring 150 is coupled to the first threaded member 154. The first actuator 128, in some examples, includes a notch 128A that is complementarily sized and shaped to accept a key 150A of the first drive ring 150, such that, with the first drive ring 150 disposed within an opening 128B of the first actuator 128, the key 150A interacts with the notch 128A to inhibit relative rotation between the first actuator 128 and the first drive ring 150. In some examples, the first drive ring 150 can be similarly coupled with a keyed configuration to the first threaded member 154 to inhibit relative rotation between the first drive ring 150 and the first threaded member 154. In this way, in some examples, rotation of the first actuator 128 can cause rotation of the first threaded member 154.

In some examples, the handle mechanism 140 includes a first drive nut 158 theadably coupled to the first threaded member 154. In some examples, the first drive nut 158 includes a substantially semi-tubular shape configured to partially wrap around the first threaded member 154 with at least one thread 158B disposed on an inside surface of the first drive nut 158 and sized and shaped to threadably engage with the at least one thread 154A of the first threaded member 154. In some examples, the first drive nut 158 is constrained from rotating when threadably coupled to the first threaded member 154 and disposed in place within the interior 104C of the handle 104. In further examples, the handle 104 includes a ridge 104D or other interior surface feature configured to abut or otherwise interact with the first drive nut 158 to inhibit the first drive nut 158 from rotating within the handle 104. In this way, in some examples, rotation of the first threaded member 154 (for instance, via rotation or other actuation of the first actuator 128) causes translation of the first drive nut 158 along the longitudinal axis 105 of the handle 104 as the at least one thread 154A rotates and, through interaction with the at least one thread 158B of the first drive nut 158, imparts translational motion to the first drive nut 158 within the handle 104.

In some examples, the first and second pullwires 167, 169 are operably coupled to first drive nut 158, such that, with rotation of the first threaded member 154, the first drive nut 158 translates along the longitudinal axis 105 of the handle 104 and, in turn, causes tension in at least one of the first pullwire 167 and the second pullwire 169. For instance, in some examples, the first and second pullwires 167, 169 are coupled to first and second pullwire blocks 166, 168, respectively. In some examples, ends of the first and second pullwires 167, 169 are respectively coupled to the first and second pullwire blocks 166, 168. In some examples, the first and second pullwire blocks 166, 168 are disposed within the interior 104C of the handle 104 and on opposite sides of an abutment 158A of the first drive nut 158. In some examples, the first pullwire block 166 is disposed on a proximal side of the abutment 158A with the first pullwire 167 extending distally from the first pullwire block 166, and the second pullwire block 168 is disposed on a distal side of the abutment 158A with the second pullwire 169 extending proximally from the second pullwire block 168. In this way, in some examples, proximal translation of the first drive nut 158 along the longitudinal axis 105 of the handle 104 causes the abutment 158A of the first drive nut 158 to abut and push the first pullwire block 166 in a proximal direction, thereby causing tension in the first pullwire 167. Additionally, in some examples, distal translation of the first drive nut 158 along the longitudinal axis 105 of the handle 104 causes the abutment 158A of the first drive nut 158 to abut and push the second pullwire block 168 in a distal direction, thereby causing tension in the second pullwire 169. The first pullwire 167, in some examples, runs directly from the elongate shaft 108 through a first through hole in the abutment 158A of the first drive nut 158 from the distal side of the abutment 158A. The first pullwire block 166 can then be threaded over and tightened down onto the first pullwire 167 on the proximal side of the abutment 158A of the first drive nut 158, allowing the first pullwire 167 to be tensioned when the first drive nut 158 is translated proximally along the longitudinal axis 105 of the handle 104 while remaining without load when the first drive nut 158 is translated distally along the longitudinal axis 105 of the handle 104.

Because the second pullwire 169 ultimately extends distally down the elongate shaft 108 to proximate the distal tip 108A of the elongate shaft 108, in some examples, the second pullwire 169, which initially extends proximally from the second pullwire block 168, needs to change direction. To that end, in some examples, a change of direction member can be used to route the second pullwire 169 from a proximally extending direction to a distally extending direction. In various examples, the change of direction member can take various forms, including, but not limited to, a pulley; a substantially U-shaped channel, member, or other such structure; a pin, a rod, or another similar structure; a substantially U-shaped tube; or the like. In some examples, a first U-shaped member 162 is configured to change a direction of the second pullwire 169, such that the second pullwire 169 initially extends proximally from the second pullwire block 168 and/or the first drive nut 158 to the first U-shaped member 162. From there, the second pullwire 169 extends around the first U-shaped member 162 and then distally from the first U-shaped member 162 to proximate the distal tip 108A of the elongate shaft 108. In this way, by translating the first drive nut 158 proximally within the handle 104 along the longitudinal axis 105, the first pullwire 167 can be put under tension, and, by translating the first drive nut 158 distally within the handle 104 along the longitudinal axis 105, the second pullwire 169 can be put under tension. In some examples, the first U-shaped member 162 is formed from a tube, such as, but not limited to, a hypotube, that is formed into substantially a U-shape. The second pullwire 169, in some examples, extends proximally from the second pullwire block 168, through a lumen of the first U-shaped member 162, and then distally from the first U-shaped member 162 through the elongate shaft 108 to proximate the distal tip 108A of the elongate shaft 108. In some examples, once the second pullwire 169 exits the elongate shaft 108, the second pullwire 169 is routed through the first U-shaped member 162 (for instance, a curved hypotube). In some examples, a composite tubing jacket can be used to shield the second pullwire 169 within the first U-shaped member 162. In some examples, the composite tubing jacket can include a lubricious inner surface to reduce friction on the second pullwire 169. In some examples, the second pullwire 169 can include a braid reinforcement to maintain durability and wear resistance. The second pullwire 169, in some examples, then runs through a second through hole on the proximal face of the abutment 158A of the first drive nut 158. On the distal side of the second through hole, in some examples, the second pullwire block 168 can be threaded over the second pullwire 169 and tightened onto the second pullwire 169, thereby locking the second pullwire 169 in place. Such a configuration, in some examples, allows the second pullwire 169 to be tensioned when the first drive nut 158 is translated distally along the longitudinal axis 105 of the handle 104 while remaining without load when the first drive nut 158 is translated proximally along the longitudinal axis 105 of the handle 104.

In some examples, the handle mechanism 140 includes a second threaded member 174 disposed within the handle 104 and movable with actuation of the second actuator 132. In some examples, the second threaded member 174 includes at least one thread 174A disposed in an outer surface of the second threaded member 174. The second threaded member 174, in some examples, is operably coupled to the third and fourth pullwires 187, 189, such that movement of the second threaded member 174 causes tension in at least one of the third pullwire 187 and the fourth pullwire 189. In some examples, rotation of the second actuator 132 causes rotation of the second threaded member 174. In some examples, the second actuator 132 is coupled directly to the second threaded member 174. In some examples, the second actuator 132 is coupled to a second drive ring 170, and the second drive ring 170 is coupled to the second threaded member 174. The second actuator 132, in some examples, includes a notch 132A that is complementarily sized and shaped to accept a key 170A of the second drive ring 170, such that, with the second drive ring 170 disposed within an opening 132B of the second actuator 132, the key 170A interacts with the notch 132A to inhibit relative rotation between the second actuator 132 and the second drive ring 170. In some examples, the second drive ring 170 can be similarly coupled with a keyed configuration to the second threaded member 174 to inhibit relative rotation between the second drive ring 170 and the second threaded member 174. In this way, in some examples, rotation of the second actuator 132 can cause rotation of the second threaded member 174. In some examples, the second drive wheel 170 is attached to a distal lock 126, which, in turn, is coupled to the distal support 124. In this way, in some examples, the distal lock 126 allows rotation of the second actuator 132, the distal lock 126 and the second drive ring 170 around the distal support 124 but inhibits distal or proximal movement of the second actuator 132, the distal lock 126 and the second drive ring 170 relative the handle 104 and the first actuator 128. In some examples, the distal lock 126 includes a first distal lock portion 126A and a second distal lock portion 126B that are engageable together to form the distal lock 126, for instance, to facilitate assembly of the handle mechanism 140.

In some examples, the handle mechanism 140 includes a second drive nut 178 theadably coupled to the second threaded member 174. In some examples, the second drive nut 178 includes a substantially semi-tubular shape configured to partially wrap around the second threaded member 174 with at least one thread 178B disposed on an inside surface of the second drive nut 178 and sized and shaped to threadably engage with the at least one thread 174A of the second threaded member 174. In some examples, the second drive nut 178 is constrained from rotating when threadably coupled to the second threaded member 174 and disposed in place within the interior 104C of the handle 104. In further examples, one or more catches 179 or other structures are included within the handle 104 and configured to abut or otherwise interact with the second drive nut 178 to inhibit the second drive nut 178 from rotating within the handle 104. In some examples, the second drive nut 178 abuts two catches 179 to constrain the second drive nut 178 from rotating within the handle 104. In this way, in some examples, rotation of the second threaded member 174 (for instance, via rotation or other actuation of the second actuator 132) causes translation of the second drive nut 178 along the longitudinal axis 105 of the handle 104 as the at least one thread 174A rotates and, through interaction with the at least one thread 178B of the second drive nut 178, imparts translational motion to the first drive nut 178 within the handle 104.

In some examples, the third and fourth pullwires 187, 189 are operably coupled to second drive nut 178, such that, with rotation of the second threaded member 174, the second drive nut 178 translates along the longitudinal axis 105 of the handle 104 and, in turn, causes tension in at least one of the third pullwire 187 and the fourth pullwire 189. For instance, in some examples, the third and fourth pullwires 187, 189 are coupled to third and fourth pullwire blocks 186, 188, respectively. In some examples, ends of the third and fourth pullwires 187, 189 are respectively coupled to the third and fourth pullwire blocks 186, 188. In some examples, the third and fourth pullwire blocks 186, 188 are disposed within the interior 104C of the handle 104 and on opposite sides of an abutment 178A of the second drive nut 178. In some examples, the third pullwire block 186 is disposed on a proximal side of the abutment 178A with the third pullwire 187 extending distally from the third pullwire block 186, and the fourth pullwire block 188 is disposed on a distal side of the abutment 178A with the fourth pullwire 189 extending proximally from the fourth pullwire block 188. In this way, in some examples, proximal translation of the second drive nut 178 along the longitudinal axis 105 of the handle 104 causes the abutment 178A of the second drive nut 178 to abut and push the third pullwire block 186 in a proximal direction, thereby causing tension in the third pullwire 187. Additionally, in some examples, distal translation of the second drive nut 178 along the longitudinal axis 105 of the handle 104 causes the abutment 178A of the second drive nut 178 to abut and push the fourth pullwire block 188 in a distal direction, thereby causing tension in the fourth pullwire 189. The third pullwire 187, in some examples, runs directly from the elongate shaft 108 through a first through hole in the abutment 178A of the second drive nut 178 from the distal side of the abutment 178A. The third pullwire block 186 can then be threaded over and tightened down onto the third pullwire 187 on the proximal side of the abutment 178A of the second drive nut 178, allowing the third pullwire 187 to be tensioned when the second drive nut 178 is translated proximally along the longitudinal axis 105 of the handle 104 while remaining without load when the second drive nut 178 is translated distally along the longitudinal axis 105 of the handle 104.

Because the fourth pullwire 189 ultimately extends distally down the elongate shaft 108 to proximate the distal tip 108A of the elongate shaft 108, in some examples, the fourth pullwire 189, which initially extends proximally from the fourth pullwire block 188, needs to change direction. To that end, in some examples, a change of direction member can be used to route the fourth pullwire 189 from a proximally extending direction to a distally extending direction. In various examples, the change of direction member can take various forms, including, but not limited to, a pulley; a substantially U-shaped channel, member, or other such structure; a pin, a rod, or another similar structure; a substantially U-shaped tube; or the like. In some examples, a second U-shaped member 182 is configured to change a direction of the fourth pullwire 189, such that the fourth pullwire 189 initially extends proximally from the fourth pullwire block 188 and/or the second drive nut 178 to the second U-shaped member 182. From there, the fourth pullwire 189 extends around the second U-shaped member 182 and then distally from the second U-shaped member 182 to proximate the distal tip 108A of the elongate shaft 108. In this way, by translating the second drive nut 178 proximally within the handle 104 along the longitudinal axis 105, the third pullwire 187 can be put under tension, and, by translating the second drive nut 178 distally within the handle 104 along the longitudinal axis 105, the fourth pullwire 189 can be put under tension. In some examples, the second U-shaped member 182 is formed from a tube, such as, but not limited to, a hypotube, that is formed into substantially a U-shape. The fourth pullwire 189, in some examples, extends proximally from the fourth pullwire block 188, through a lumen of the second U-shaped member 182, and then distally from the second U-shaped member 182 through the elongate shaft 108 to proximate the distal tip 108A of the elongate shaft 108.

In some examples, once the fourth pullwire 189 exits the elongate shaft 108, the fourth pullwire 189 is routed through the second U-shaped member 182 (for instance, a curved hypotube). In some examples, a composite tubing jacket can be used to shield the fourth pullwire 189 within the second U-shaped member 182. In some examples, the composite tubing jacket can include a lubricious inner surface to reduce friction on the fourth pullwire 189. In some examples, the fourth pullwire 189 can include a braid reinforcement to maintain durability and wear resistance. The fourth pullwire 189, in some examples, then runs through a second through hole on the proximal face of the abutment 178A of the second drive nut 178. On the distal side of the second through hole, in some examples, the fourth pullwire block 188 can be threaded over the fourth pullwire 189 and tightened onto the fourth pullwire 189, thereby locking the fourth pullwire 189 in place. Such a configuration, in some examples, allows the fourth pullwire 189 to be tensioned when the second drive nut 178 is translated distally along the longitudinal axis 105 of the handle 104 while remaining without load when the second drive nut 178 is translated proximally along the longitudinal axis 105 of the handle 104.

In some examples, the first threaded member 154 at least partially overlaps the second threaded member 174, such that the second threaded member 174 is disposed at least partially within the first threaded member 154. In this way, in some examples, use of space within the interior 104 can be substantially optimized in order to keep an overall size of the handle 104 relatively small and manageable by the physician or other user. In some examples, the second threaded member 174 rotates around the support tube 120 with actuation of the second actuator 132. The first threaded member 154, in some examples, rotates around the second threaded member 174 and/or the second drive nut 178 with actuation of the first actuator 128. In this way, in some examples, multidirectional control of the distal tip 108A can be achieved, and the relatively numerous components of the handle mechanism 140 to achieve such multidirectional control can be fit within the confines of the interior 104C of the handle 104, while keeping the size of the handle 104 relatively manageable by the physician or other user, without interference between various components of the handle mechanism 140.

Figure 10:
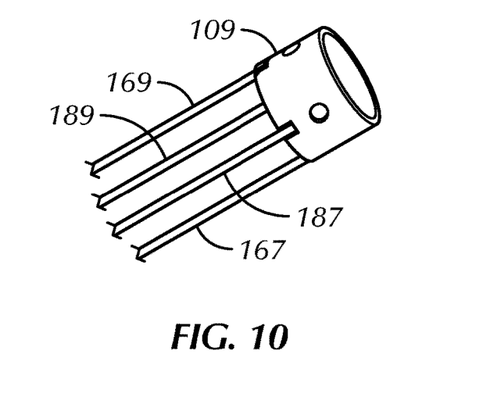
FIG. 10 is a perspective view of a pullwire connection ring of the steerable medical device of FIG. 1.

Referring to FIG. 10, the pullwire ring 109, in some examples, can be disposed proximate the distal tip 108A of the elongate shaft 108. In various examples, the pullwire ring 109 can be adhered to, molded into, welded to, or otherwise attached to the elongate shaft 108 proximate the distal tip 108A of the elongate shaft 108. In some examples, the first, second, third, and fourth pullwires 167, 169, 187, 189 are attached to the pullwire ring 109. In various examples, the first, second, third, and fourth pullwires 167, 169, 187, 189 can be attached to the pullwire ring 109 by welding, soldering, brazing adhesive, mechanical fastener, or a combination thereof. In some examples, the first, second, third, and fourth pullwires 167, 169, 187, 189 are equidistantly spaced around the pullwire ring 109 from one another. In some examples, the first and second pullwires 167, 169 are spaced around the pullwire ring 109 substantially 180 degrees from one another. In some examples, the third and fourth pullwires 187, 189 are spaced around the pullwire ring 109 substantially 180 degrees from one another.

Figure 11:
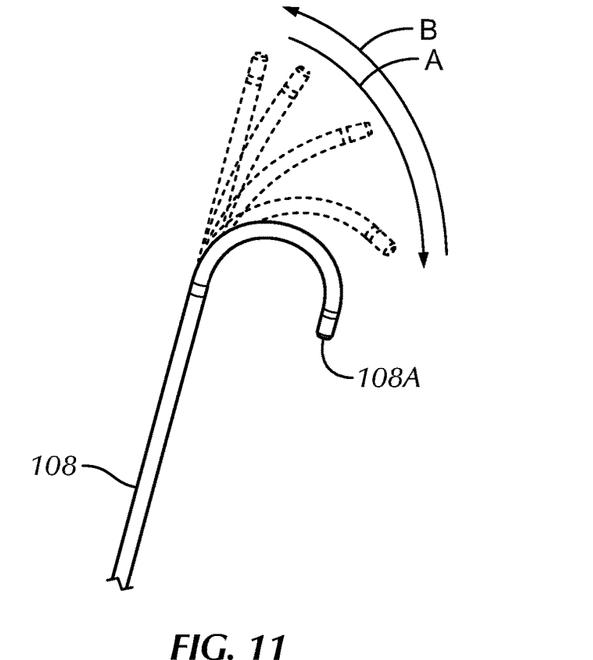
FIG. 11 is a perspective view of movement of a tip of the steerable medical device of FIG. 1 with actuation of a one control in one direction.
Figure 12:
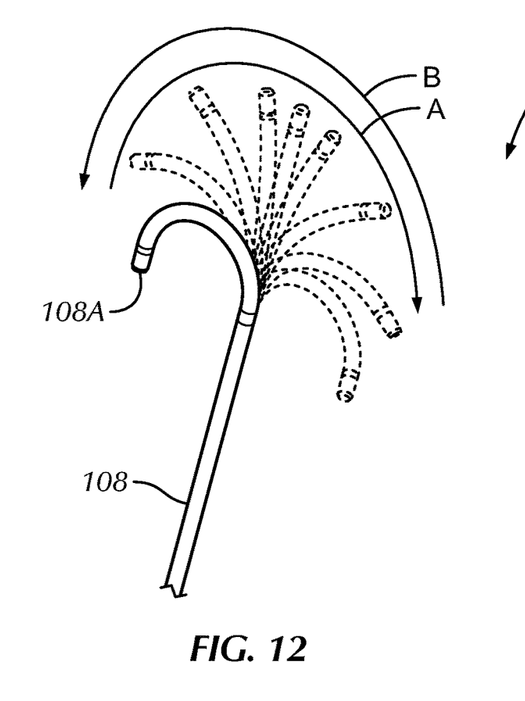
FIG. 12 is a perspective view of movement of the tip of the steerable medical device of FIG. 1 with actuation of a one control in both directions.
Figure 13:
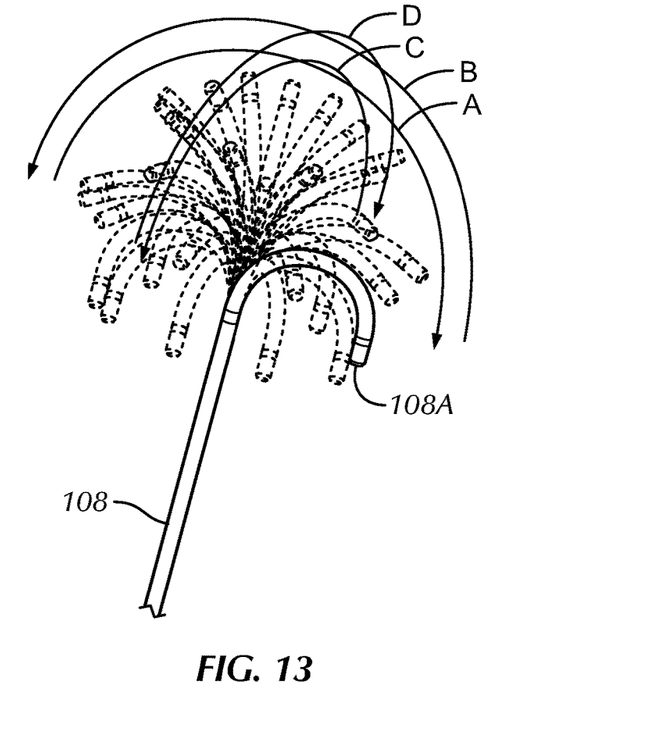
FIG. 13 is a perspective view of movement of the tip of the steerable medical device of FIG. 1 with actuation of both controls in both directions.

Referring now to FIGS. 11-13, various examples of deflection of the distal tip 108A of the elongate shaft 108 are shown. Through actuation of one or both of the first and second actuators 128, 132, various positions of the distal tip 108A of the elongate shaft 108 can be achieved. For instance, in some examples, actuation of the first actuator 128 in a first actuator direction causes tension in the first pullwire 167 and deflection of the distal tip 108A in a first tip direction A. In further examples, actuation of the first actuator 128 in a second actuator direction causes tension in the second pullwire 169 and deflection of the distal tip 108A in a second tip direction B substantially opposite the first tip direction A. In some examples, rotation of the first actuator 128 in a first rotational direction (for instance, counterclockwise) causes tension in the first pullwire 167 to deflect the distal tip 108A in the first tip direction A, and rotation of the first actuator 128 in a second rotational direction (for instance, clockwise) causes tension in the second pullwire 169 to deflect the distal tip 108A in the second tip direction B. In further examples, actuation of the second actuator 132 in a first actuator direction causes tension in the third pullwire 187 and deflection of the distal tip 108A in a third tip direction C different from the first tip direction A and the second tip direction B. In still further examples, actuation of the second actuator 132 in a second actuator direction causes tension in the fourth pullwire 189 and deflection of the distal tip 108A in a fourth tip direction D substantially opposite the third tip direction C. In some examples, rotation of the second actuator 132 in a first rotational direction (for instance, counterclockwise) causes tension in the third pullwire 187 to deflect the distal tip 108A in the third tip direction C, and rotation of the second actuator 132 in a second rotational direction (for instance, clockwise) causes tension in the fourth pullwire 189 to deflect the distal tip 108A in the fourth tip direction D. Referring specifically to FIG. 13, in some examples, by actuating each of the first and second actuators 128, 132, the elongate shaft 108 can be deflected in various ways and a plurality of positions of the distal tip 108A can be achieved. As demonstrated in FIG. 13, substantially any position of the distal tip 108A can be achieved within a spherical area at the distal end of the elongate shaft 108A. In this way, such maneuverability can facilitate navigation of the distal tip 108A and/or the elongate shaft 108 within the patient and, once in place within the patient, articulation of the distal tip 108A in substantially any direction to facilitate any of various procedures intended to be performed by the device 100 or with assistance from the device 100.

Referring back to FIG. 2, the placement of the first and second actuators 128, 132, in some examples, allows for one-handed operation by the physician or other user. That is, having both the first actuator 128 and the second actuator 132 at the distal end of the handle 104, the physician or other user can hold onto the handle 104 with one hand and use a thumb and/or a finger (for instance, the index finger) to control each of the first and second actuators 128, 132. One-handed control of the device 100 is advantageous in that it frees up the other hand of the physician or other user to do other things and/or control other devices during the procedure for which the device 100 is being used. Moreover, each of the first and second actuators 128, 132 can be actuated independently without interfering with the actuation of the other of the first and second actuators 128, 132. This is achieved, in some examples, by constraining each of the first and second actuators 128, 132 from translating during rotation of the first and second actuators 128, 132, as described herein. Additionally, actuation of the various components of the handle mechanism 140 associated with the first actuator 128 can be accomplished without impacting actuation of the various components of the handle mechanism 140 associated with the second actuator 132 and vice versa. For instance, translating the first drive nut 158 does not affect translating the second drive nut 178 and vice versa. In this way, independent control of the first and second actuators 128, 132 can be achieved.

In some examples, the four pullwires 167, 169, 187, 189 can be tensioned at different rates using the first and second actuators 128, 132 to provide distal tip 108A deflection in substantially 360 degrees. Additionally, in some examples, the handle mechanism 140 enables substantially 360-degree steering of the elongate shaft 108 of the device by using only two sliding components (the first and second drive nuts 158, 178) within the handle 104. Having only two sliding members can allow for more/easier control over the location of the pullwire blocks 166, 168, 186, 188 which can impact the amount of "dead zone" when at least one of the first and second actuators is rotated (the amount of rotation in which neither pullwire associated with that actuator is engaged). Minimizing such "dead zone" can be advantageous.

In some examples, by using two U-shaped members 162, 182 (for instance, two curved hypotube segments), two pullwires 169, 189 of the four pullwires 167, 169, 187, 189 are redirected substantially 180 degrees, which reverses the direction of the pull required to activate these two wires 169, 189. This allows each of the two independent sliding components (the first and second drive nuts 158, 178) to each be used on a pair of pullwires (pullwires 167, 169 for the first drive nut 158 and pullwires 187, 189 for the second drive nut 178). Each sliding component 158, 178 is independently mated to the respective actuator 128, 132. In this way, the distal tip 108A can achieve a full range of deflection/steering through a coordinated rotation of each of the first and second actuators 128, 132.

The present inventors have recognized various advantages of the subject matter described herein. For instance, in some examples, the examples of devices, apparatuses, systems, and methods described herein can be used to provide multidirectional steering capability. In some examples, the subject matter described herein can provide multiple degrees of motion to a medical device to allow for increased maneuverability within a patient. In various examples, the device, apparatus, system, and method can be used to provide a device with multiple degrees of motion to allow for a tip of the device to have a 360-degree range of deflection. Such a device is further advantageous, in some examples, since such a range of deflection can be achieved using one hand to steer the distal end of the medical device, thereby freeing the other hand for other things, such as controlling another device used in the procedure. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A steerable medical device comprising:
   a handle including a longitudinal axis;
   an elongate shaft extending distally from the handle, the elongate shaft including a distal tip and a lumen through the elongate shaft;
   at least four pullwires disposed within the handle and extending to and anchored proximate the distal tip of the elongate shaft, the at least four pullwires including a first pullwire, a second pullwire, a third pullwire, and a fourth pullwire;
   at least two actuators associated with the handle, the at least two actuators including a first actuator and a second actuator, the first actuator being operably coupled to the first and second pullwires and the second actuator being operably coupled to the third and fourth pullwires, wherein:
      actuation of the first actuator in a first actuator direction causes tension in the first pullwire and deflection of the distal tip in a first tip direction;
      actuation of the first actuator in a second actuator direction causes tension in the second pullwire and deflection of the distal tip in a second tip direction substantially opposite the first tip direction;
      actuation of the second actuator in the first actuator direction causes tension in the third pullwire and deflection of the distal tip in a third tip direction different from the first tip direction and the second tip direction; and
      actuation of the second actuator in the second actuator direction causes tension in the fourth pullwire and deflection of the distal tip in a fourth tip direction substantially opposite the third tip directions;
   a first threaded member disposed within the handle and movable with the actuation of the first actuator in either the first actuator direction or the second actuator direction, the first threaded member being operably coupled to the first and second pullwires, wherein movement of the first threaded member causes the tension in at least one of the first pullwire and the second pullwire; and
   a second threaded member disposed within the handle and movable with the actuation of the second actuator in either the first actuator direction or the second actuator direction, the second threaded member being operably coupled to the third and fourth pullwires, wherein movement of the second threaded member causes the tension in at least one of the third pullwire and the fourth pullwire; wherein the first threaded member at least partially overlaps the second threaded member, the second threaded member being disposed at least partially within the first threaded member, the first and second threaded members being independently actuatable with respect to one another.

2. The steerable medical device of claim 1, wherein the at least four pullwires extend within the elongate shaft to proximate the distal tip of the elongate shaft.

3. The steerable medical device of claim 1, wherein the first actuator is rotatable about the longitudinal axis of the handle.

4. The steerable medical device of claim 1, wherein the second actuator is rotatable about the longitudinal axis of the handle.

5. The steerable medical device of claim 1, wherein the first actuator and the second actuator are each independently rotatable about the longitudinal axis of the handle.

6. The steerable medical device of claim 1, wherein the actuation of the first actuator in either the first actuator direction or the second actuator direction causes rotation of the first threaded member.

7. The steerable medical device of claim 6, comprising a first drive nut theadably coupled to the first threaded member, the first and second pullwires being operably coupled to the first drive nut, wherein the rotation of the first threaded member causes translation of the first drive nut along the longitudinal axis of the handle and, in turn, the tension in at least one of the first pullwire and the second pullwire.

8. The steerable medical device of claim 7, wherein a proximal translation of the first drive nut causes the tension in the first pullwire and a distal translation of the first drive nut causes the tension in the second pullwire.

9. The steerable medical device of claim 8, comprising a first U-shaped member configured to change a direction of the second pullwire, the second pullwire extending:
   proximally from the first drive nut to the first U-shaped member;
   around the first U-shaped member; and
   distally from the first U-shaped member to proximate the distal tip of the elongate shaft.

10. The steerable medical device of claim 8, comprising first and second pullwire blocks are disposed on opposite sides of an abutment of the first drive nut, the first pullwire block being disposed on a proximal side of the abutment with the first pullwire extending distally from the first pullwire block, the second pullwire block being disposed on a distal side of the abutment with the second pullwire extending proximally from the second pullwire block, wherein:
   the proximal translation of the first drive nut causes the abutment of the first drive nut to abut and push the first pullwire block in a proximal direction, thereby causing the tension in the first pullwire; and
   the distal translation of the first drive nut causes the abutment of the first drive nut to abut and push the second pullwire block in a distal direction, thereby causing the tension in the second pullwire.

11. The steerable medical device of claim 1, wherein actuation of the second actuator in either the first actuator direction or the second actuator direction causes rotation of the second threaded member.

12. The steerable medical device of claim 11, comprising a second drive nut theadably coupled to the second threaded member, the third and fourth pullwires being operably coupled to the second drive nut, wherein the rotation of the second threaded member causes the translation of the second drive nut along the longitudinal axis of the handle and, in turn, the tension in at least one of the third pullwire and the fourth pullwire.

13. The steerable medical device of claim 12, wherein a proximal translation of the second drive nut causes the tension in the third pullwire and a distal translation of the second drive nut causes the tension in the fourth pullwire.

14. The steerable medical device of claim 13, comprising a second U-shaped member configured to change a direction of the fourth pullwire, the fourth pullwire extending:
   proximally from the second drive nut to the second U-shaped member;
   around the second U-shaped member; and
   distally from the second U-shaped member to proximate the distal tip of the elongate shaft.

15. The steerable medical device of claim 1, comprising a support tube including at least one window within a sidewall of the support tube, wherein the first, second, third, and fourth pullwires extend out of the elongate shaft and into the support shaft, the first, second, third, and fourth pullwires extending from the at least one window to operably couple with the first and second actuators.

16. The steerable medical device of claim 1, comprising a first drive ring coupled to the first threaded member, wherein the first actuator includes a notch that is complementarily sized and shaped to accept a key of the first drive ring, the key interacting with the notch to inhibit relative rotation between the first actuator and the first drive ring.

17. A steerable medical device comprising:
   a handle including a longitudinal axis;
   an elongate shaft extending distally from the handle, the elongate shaft including a distal tip and a lumen through the elongate shaft;
   at least four pullwires disposed within the handle and extending to and anchored proximate the distal tip of the elongate shaft, the at least four pullwires including a first pullwire, a second pullwire, a third pullwire, and a fourth pullwire;
   at least two actuators associated with the handle, the at least two actuators including a first actuator and a second actuator;
   at least two threaded members disposed within the handle, the at least two threaded members including a first threaded member and a second threaded member, the first threaded member being movable with actuation of the first actuator, and the second threaded member being movable with actuation of the second actuator, wherein the first threaded member at least partially overlaps the second threaded member, the second threaded member being disposed at least partially within the first threaded member, the first and second threaded members being independently actuatable with respect to one another; and
   at least two drive nuts disposed within the handle, the at least two drive nuts including a first drive nut and a second drive nut, the first drive nut being theadably coupled to the first threaded member and translatable along the longitudinal axis of the handle with movement of the first threaded member, the second drive nut being theadably coupled to the second threaded member and translatable along the longitudinal axis of the handle with movement of the second threaded member, the first and second pullwires being operably coupled to the first drive nut, and the third and fourth pullwires being operably coupled to the second drive nut, wherein:
      the actuation of the first actuator in a first actuator direction causes tension in the first pullwire and deflection of the distal tip in a first tip direction;
      the actuation of the first actuator in a second actuator direction causes tension in the second pullwire and deflection of the distal tip in a second tip direction substantially opposite the first tip direction;

the actuation of the second actuator in the first actuator direction causes tension in the third pullwire and deflection of the distal tip in a third tip direction different from the first tip direction and the second tip direction; and the actuation of the second actuator in the second actuator direction causes tension in the fourth pullwire and deflection of the distal tip in a fourth tip direction substantially opposite the third tip direction.

18. The steerable medical device of claim 17, wherein:

a proximal translation of the first drive nut causes the tension in the first pullwire and a distal translation of the first drive nut causes the tension in the second pullwire; and a proximal translation of the second drive nut causes the tension in the third pullwire and a distal translation of the second drive nut causes the tension in the fourth pullwire.

19. The steerable medical device of claim 17, wherein the first actuator and the second actuator are each independently rotatable about the longitudinal axis of the handle.

20. The steerable medical device of claim 17, comprising a support tube including at least one window within a sidewall of the support tube, wherein the first, second, third, and fourth pullwires extend out of the elongate shaft and into the support shaft, the first, second, third, and fourth pullwires extending from the at least one window to operably couple with the first and second actuators.

* * * * *